United States Patent
Wang et al.

(10) Patent No.: US 11,465,971 B2
(45) Date of Patent: Oct. 11, 2022

(54) METHOD FOR PREPARING MESACONINE AND RELATED INTERMEDIARIES THEREOF

(71) Applicant: Gooddoctor Pharmaceutical Group Co., Ltd., Sichuan (CN)

(72) Inventors: Fengpeng Wang, Sichuan (CN); Yuefei Geng, Sichuan (CN); Xixian Jian, Sichuan (CN); Donglin Chen, Sichuan (CN); Funeng Geng, Sichuan (CN)

(73) Assignee: Gooddoctor Pharmaceutical Group Co., Ltd.

( * ) Notice: Subject to any disclaimer, the term of this patent is extended or adjusted under 35 U.S.C. 154(b) by 253 days.

(21) Appl. No.: 16/963,973

(22) PCT Filed: Jan. 23, 2019

(86) PCT No.: PCT/CN2019/072873
§ 371 (c)(1),
(2) Date: Jul. 22, 2020

(87) PCT Pub. No.: WO2019/144888
PCT Pub. Date: Aug. 1, 2019

(65) Prior Publication Data
US 2021/0040042 A1 Feb. 11, 2021

(30) Foreign Application Priority Data
Jan. 24, 2018 (CN) .......................... 201810071927.2

(51) Int. Cl.
*C07D 221/22* (2006.01)
(52) U.S. Cl.
CPC ........ *C07D 221/22* (2013.01); *C07B 2200/13* (2013.01)
(58) Field of Classification Search
CPC .................................................. C07D 221/22
See application file for complete search history.

(56) References Cited

U.S. PATENT DOCUMENTS 10,941,116 B2 * 3/2021 Geng .................... C07D 221/22

FOREIGN PATENT DOCUMENTS

| CN | 101759640 A | | 6/2010 |
| CN | 102146057 | * | 8/2011 |
| CN | 102146057 A | | 8/2011 |
| CN | 102146057 B | | 11/2012 |
| CN | 102977020 A | | 3/2013 |
| DE | 19511235 A1 | | 10/1996 |

OTHER PUBLICATIONS

Caira, Crystalline Polymorphism of Organic Compounds, Topics in Current Chemistry, 1998, pp. 163-208, vol. 198.
Extended European Search Report including Written Opinion for EP19743594.4 dated Jun. 4, 2021; 10 pages.
Sakai, S. et al, Partial Synthesis of Isodelphinine and Penduline, Yakugaku Zasshi, received Jan. 30, 1984, vol. 104, No. 7, XP055627143 (English abstract provided), pp. 731-752; Conversion of 31 to mesaconine; p. 740.
Sakai, S. et al, Partial Synthesis of Isodelphinine and Penduline, Yakugaku Zasshi, received Jan. 1984, pp. 747-748, vol. 104, No. 7, ISSN: 0031-6903. (English abstract provided).
Morio, S.I., Aconitum Alkaloids. VI. Mesaconitine, a Second New Aconitum Alkaloid, Justus Liebigs Annalen der Chemie, Dec. 1929, pp. 189-190, ISSN: 0075-4617. (Abstract only).
International Search Report for Application No. PCT/CN2019/072874, dated Apr. 15, 2019, pp. 1-2.
Jian, et al., Structure-Cardiac Activity Relationship of C19-Diterpenoid Alkaloids, Natural Product Communications, accepted Apr. 2012, pp. 713-720, vol. 7, No. 6.
Zhang, et al., Further Studies on Structure-Cardiac Activity Relationships of Diterpenoid Alkaloids, Natural Product Communications, accepted Aug. 2015, pp. 2075-2084, vol. 10, No. 12.
Aconitum carmichaeli Debx., vol. 1, the Chinese Pharmacopoeia, 2015 edition, pp. 191-193.
Determination method of the melting point, the first method of 0612, general rule, vol. 4, The Chinese Pharmacopoeia, 2015 Edition, pp. 75-76.
Guiding principle for stability test of raw materials of drugs and preparations, general rule 9001, the Chinese Pharmacopoeia, 2015 edition, pp. 354-356.
The method of solubility test in the Chinese Pharmacopoeia, 2015 edition, general notice, pp. 378-379.
The definition of hygroscopicity in Chinese Pharmacopoeia, general rule 9103, vol. 4, 2015 Edition, pp. 378-379.
Xiu-Xiu Liu et al., "Cardioactive C19-Diterpenoid Alkaloids from the Lateral Roots of Aconitum carmichaeli "Fu Zi"," Chem. Pharm Bull. vol. 60 (1), Jan. 2012, pp. 144-149.
Tsuda Y, Achmatowicz Jr O, Marion L. Hypaconitin (Desoxymesaconitin) und Desoxyaconitin. Justus Liebigs Annalen der Chemie. Dec. 1964;680(1):88-92.
Zhou, Yuanpeng, "Detoxification of Prepared Common Monkshood Branched Root from the Hydrolyis of Diester-type Alkaloids (2))" Pharmacology and Clinics of Chinese Materia Medica, vol. 3 (30), Jun. 15, 2014, pp. 154-157.
Wu, Ping, "Study on Extraction, Isolation, and Hydrolyis Law of Prepared Common Monkshood Branched Root Alkaloids," Thesis of Chengdu University of TCM, May 1, 2007, 74 pages.
International Search Report for PCT/CN2019/072873 dated Apr. 30, 2019; 2 pages.

* cited by examiner

Primary Examiner — D Margaret M Seaman
(74) Attorney, Agent, or Firm — Lerner, David, Littenberg, Krumholz & Mentlik, LLP

(57) ABSTRACT

The present invention relates to a method for preparing mesaconine and related intermediaries. Specifically, in the method for preparing mesaconine of the present invention, aconitine extracted from the *Aconitum soongaricum Stapf.* of aconitum plant is used as a raw material and subjected to alkalization, acetylation, N-de-ethylation, N-methylation, and hydrolysis to obtain mesaconine. The method for preparing mesaconine in the present invention is simple in operation, high in yield, environmentally friendly and pollution-free, and suitable for industrial production.

8 Claims, No Drawings

METHOD FOR PREPARING MESACONINE AND RELATED INTERMEDIARIES THEREOF

CROSS REFERENCE TO RELATED APPLICATIONS

The present application is a national phase entry under 35 U.S.C. § 371 of International Application No. PCT/CN2019/072873, filed Jan. 23, 2019, which claims priority from Chinese Patent Application No. 201810071927.2 filed on Jan. 24, 2018, the disclosures of which are hereby incorporated herein by reference.

TECHNICAL FIELD

The invention relates to the field of synthesis, in particular to a method for preparing mesaconine and related intermediates.

TECHNICAL BACKGROUND

The traditional Chinese medicine monkshood is a processed product obtained from rootlet of *Aconitum carmichaeli* Debx., which has the effects of rescuing from collapse by restoring yang, eliminating wind-cold-dampness, warming the meridian torelieve pain (volume 1, *Chinese pharmacopoeia*, 2015 edition). And it is widely used in the clinic as a famous traditional Chinese medicine.

Studies have found that mesaconine is the main cardiotonic active ingredient of monkshood, as recorded in the following documents: Xiu-Xiu Liu, et al, *Chem. Pharm. Bull*, 2012, 60(1), 144-149; Xi-Xian Jian, et al, *Nat. Prod. Commun*, 2012, 7(6), 713-720; Chinese invention patent, 2012, CN102146057B; Zhong-Tang Zhang, et al, *Nat. Prod. Commun*, 2015, 10(12), 2075-2084. Therefore, mesaconine has a prospect of developing into anti-heart failure drugs.

Mesaconine has a chemical name of N-methyl-1α,6α,16β,18-tetramethoxyl-4-methyl-aconite-3α,8β,13β,14α,15α-pentol with a molecular formula of $C_{24}H_{39}NO_9$ and a CAS No: 6792-09-2, and has a structure represented by the following Structural Formula.

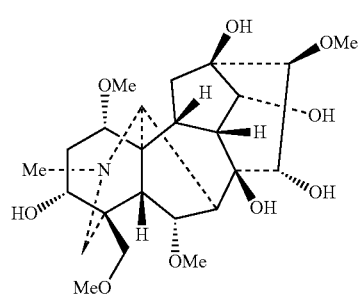

Chinese invention patent CN 102146057B discloses the preparation method of mesaconine, in which mesaconine is obtained by using aconitine from *Aconitum soongaricum Stapf.* of aconitum plant as the raw material through complete acetylation, N-deethylation, N-methylation and hydrolysis. However, this preparation method involves highly toxic aconitine and mesaconitine, which is not conducive to safe production.

In order to overcome the deficiencies of the existing technology, it is necessary to develop a preparation process of mesaconine which is simple in operation, high in yield, environmentally friendly and pollution-free, and suitable for industrialization.

SUMMARY OF THE INVENTION

The object of the present invention is to provide a preparation method of mesaconine, which is simple in operation, high in yield, environmentally friendly and pollution-free, and suitable for industrial production.

The preparation method of mesaconine of the present invention comprises the following steps:

1) dissolving aconitine (I) in ethanol (e.g., 95% ethanol), adding sodium hydroxide thereto to hydrolyze, concentrating under reduced pressure, and diluting the residue with water, extracting with dichloromethane to remove impurity alkaloids, acidifying the alkaline aqueous solution with hydrochloric acid, adjusting to pH 11 to 12 by aqua ammonia or a solution of sodium hydroxide in ethanol, concentrating under reduced pressure to dryness, dissolving the residue with dichloromethane-ethanol (6:1 to 12:1, preferably 9:1, V/V), filtering, and concentrating the filtrate under reduced pressure to obtain aconine (II);

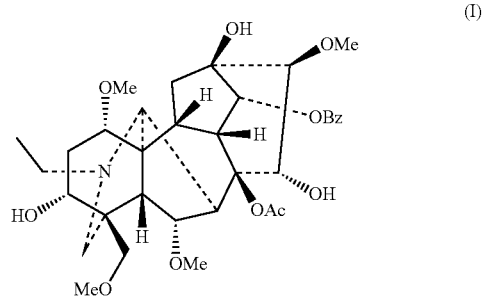

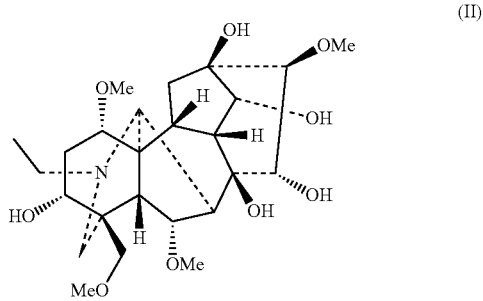

2) dissolving aconine (II) in pyridine and reacting with acetic anhydride, concentrating under reduced pressure to obtain a residue, diluting the residue with water, alkalizing with aqua ammonia, extracting with dichloromethane, combining dichloromethane layers, and then drying, concentrating, and separating by silica-gel column chromatography in sequence to prepare 3,14,15-triacetyl aconine (III);

(III)

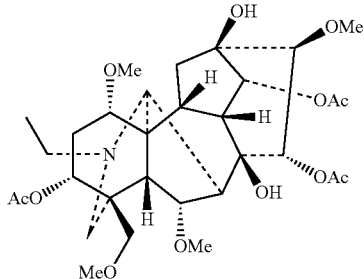

or reacting aconine (II) with acetic anhydride under the catalysis of p-toluene sulfonic acid, concentrating under reduced pressure to obtain a residue, diluting the residue with water, alkalizing with aqua ammonia, extracting with dichloromethane, combining dichloromethane layers, and then drying, concentrating, and separating by silica-gel column chromatography in sequence to prepare 3,8,13,14,15-pentaacetyl aconine (IV);

(IV)

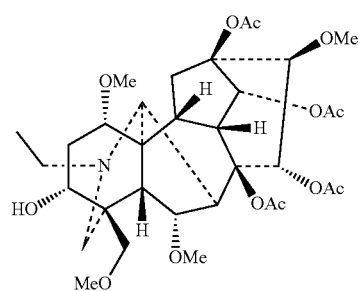

3) dissolving 3,14,15-triacetyl aconine (III) in glacial acetic acid, adding N-bromosuccinimide thereto, stirring at room temperature, concentrating under reduced pressure to obtain a residue, adding aqua ammonia to the residue, extracting with dichloromethane, combining dichloromethane extracts, drying, and concentrating under reduced pressure to prepare N-desethyl-3,14,15-triacetyl aconine (V);

(V)

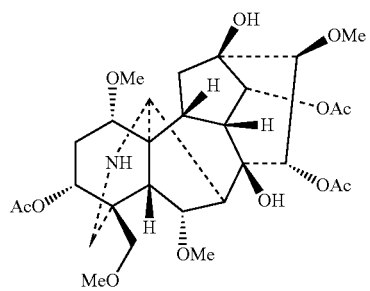

or dissolving 3,8,13,14,15-pentaacetyl aconine (IV) in glacial acetic acid, adding N-bromosuccinimide thereto, stirring at room temperature, concentrating under reduced pressure to obtain a residue, adding aqua ammonia to the residue, extracting with dichloromethane, combining dichlorometh-ane extracts, drying, and concentrating under reduced pressure to prepare N-desethyl-3,8,13,14,15-pentaacetyl aconine (VI);

(VI)

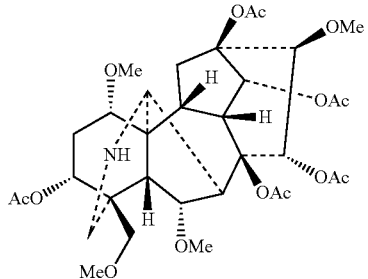

4) dissolving N-desethyl-3,14,15-triacetyl aconine (V) in tetrahydrofuran, adding formaldehyde aqueous solution and glacial acetic acid thereto at room temperature, stirring at room temperature, adding NaBH(OAc)$_3$, continuing to stir, adding aqua ammonia (adjust to pH 9 to 10), diluting with water, then extracting with dichloromethane, combining the dichloromethane extracts, and then washing with water, drying, and concentrating under reduced pressure in sequence to prepare 3,14,15-triacetylmesaconine (VII);

(VII)

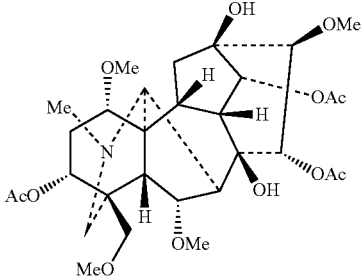

or dissolving N-desethyl-3,8,13,14,15-pentaacetyl aconine (VI) in tetrahydrofuran, adding formaldehyde aqueous solution and glacial acetic acid thereto at room temperature, stirring at room temperature, adding NaBH(OAc)$_3$, continuing to stir, adding aqua ammonia (adjust to pH 9 to 10), diluting with water, extracting with dichloromethane, combining the dichloromethane extracts, and then washing with water, drying, and concentrating under reduced pressure in sequence to prepare 3,8,13,14,15-pentaacetylmesaconine (VIII);

(VIII)

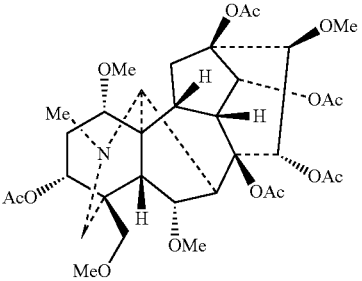

5) dissolving 3,14,15-triacetylmesaconine (VII) or 3,8,13,14,15-pentaacetylmesaconine (VIII) in ethanol (e.g., 95% ethanol) solution, adding sodium hydroxide to react with the mesaconine derivative respectively, adjusting to pH 4 to 5 with hydrochloric acid, then adjusting to pH 9 to 12 with aqua ammonia or a solution of sodium hydroxide in ethanol, filtering off insoluble materials, concentrating under reduced pressure, dissolving the residue with dichloromethane-ethanol (6:1 to 12:1, preferably 9:1, V/V), filtering with suction, and concentrating the filtrate under reduced pressure to obtain mesaconine (IX)

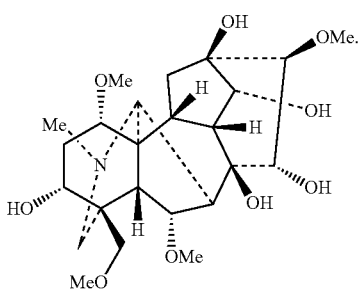

(IX)

In an embodiment of the present invention, the aconitine (I) can be prepared by the following method:

After crushing the roots of the aconitum plant, adding sulfuric acid-ethanol aqueous solution to extract under reflux; concentrating the extract under reduced pressure to obtain a solid extract; diluting the solid extract with water, and after alkalization, extracting with ethyl acetate, and recovering the solvent to obtain an ethyl acetate extract; subjecting the ethyl acetate extract to acid dissolution, filtration, and alkalization and precipitation to obtain the aconitine (I).

In an embodiment of the present invention, based on the total mass of the sulfuric acid-ethanol aqueous solution, the content of sulfuric acid can be 1-10%, the content of ethanol can be 80-90%, preferably, the content of sulfuric acid can be 5%, the content of ethanol can be 85%.

In an embodiment of the present invention, the aconitum plant can be *Aconitum soongaricum Stapf.* or *Aconitum karakolicum Rapaics.*

Furthermore, the mesaconine of the present invention is prepared by the following steps:

1) after crushing the roots of *Aconitum soongaricum Stapf.* of aconitum plant, adding an aqueous solution of 5% sulfuric acid-85% ethanol to extract under reflux; concentrating the extract under reduced pressure to obtain a solid extract; diluting the solid extract with water, and after alkalization, extracting with ethyl acetate, and recovering the solvent to obtain an ethyl acetate extract; subjecting the ethyl acetate extract to acid dissolution, filtration, and alkalization and precipitation to obtain total alkaloids, wherein the main component in the total alkaloids is aconitine (I);

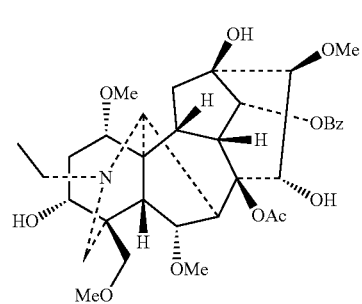

(I)

2) dissolving the total alkaloids in 95% ethanol, adding 3 to 5 times the molar amount of sodium hydroxide relative to the total amount of aconitine (I) in the total alkaloids thereto, reacting at room temperature for 1 to 2 hours, concentrating under reduced pressure to remove 95% ethanol, diluting the residue with 5 to 10 times the amount of water, extracting with dichloromethane to remove impurities alkaloids, adjusting the alkaline aqueous solution to pH 5 with hydrochloric acid, and adjusting to pH 11 to 12 with aqua ammonia or a solution of sodium hydroxide in ethanol, concentrating under reduced pressure to dryness, and dissolving the residue with dichloromethane-anhydrous ethanol (9:1, V/V), filtering, and concentrating the filtrate under reduced pressure to obtain aconine (II);

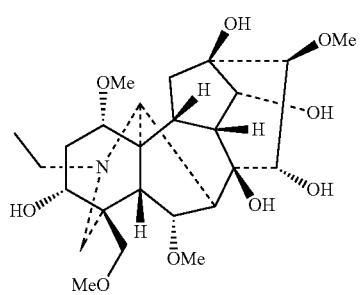

(II)

3) dissolving aconine (II) in pyridine, reacting the aconine (II) with 6 to 8 moles of acetic anhydride under reflux for 2 to 3 hours, concentrating under reduced pressure to obtain a residue, diluting the residue with water, alkalizing with aqua ammonia, extracting with dichloromethane, combining dichloromethane layers, and then drying over anhydrous sodium sulfate, concentrating, and separating by silica-gel column chromatography (dichloromethane-ethanol=200:1) in sequence to obtain 3,14,15-triacetyl aconine (III);

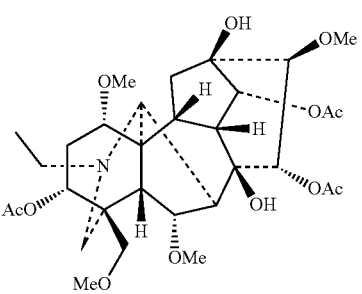

(III)

or
reacting the aconine (II) with 6 to 8 moles of acetic anhydride under reflux for 3 to 4 hours under the catalysis of p-toluene sulfonic acid, concentrating under reduced pressure to obtain a residue, diluting the residue with water, alkalizing with aqua ammonia, extracting with dichloromethane, combining dichloromethane layers, and then drying over anhydrous sodium sulfate, concentrating, and separating by silica-gel column chromatography (eluting by petroleum ether-acetone (10:1 to 2:1)) in sequence to prepare 3,8,13,14,15-pentaacetyl aconine (IV);

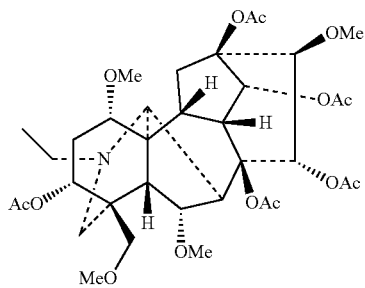
(IV)

4) dissolving 3,14,15-triacetyl aconine (III) in 10 times the amount of glacial acetic acid, reacting with 3 to 5 moles of N-bromosuccinamide at room temperature under stirring for 2 to 3 hours, concentrating under reduced pressure to obtain a residue, adjusting to pH 9 to 10 with strong aqua ammonia, extracting with dichloromethane twice, combining dichloromethane extracts, and then drying over anhydrous sodium sulfate, and concentrating under reduced pressure to obtain N-desethyl-3,14,15-triacetyl aconine (V);

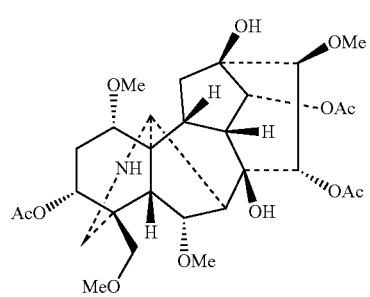
(V)

or
dissolving 3,8,13,14,15-pentaacetyl aconine (IV) in 10 times the amount of glacial acetic acid, reacting with 3 to 5 moles of N-bromosuccinamide at room temperature under stirring for 2-3 hours, concentrating under reduced pressure to obtain a residue, adjusting to pH 9 to 10 with strong aqua ammonia, extracting with dichloromethane twice, combining dichloromethane extracts, and then drying over anhydrous sodium sulfate, and concentrating under reduced pressure to obtain N-desethyl-3,8,13,14,15-pentaacetyl aconine (VI);

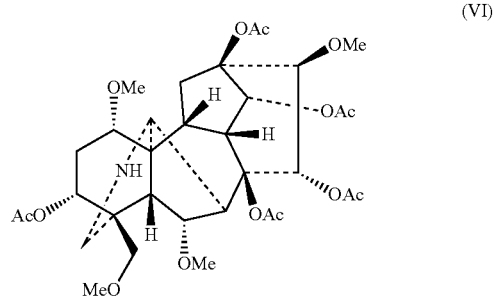
(VI)

5) dissolving N-desethyl-3,14,15-triacetyl aconine (V) in tetrahydrofuran, reacting with 12 moles of 40% formaldehyde aqueous solution and 1 to 2 moles of glacial acetic acid at room temperature under stirring for 30 to 60 minutes, adding 2 to 3 moles of sodium triacetoxyborohydride, stirring at room temperature for 30 to 60 minutes, adjusting to pH 9 to 10 with strong aqua ammonia, diluting by adding water, extracting with dichloromethane, combining the dichloromethane extracts, and then drying over anhydrous sodium sulfate, and concentrating under reduced pressure in sequence to obtain 3,14,15-triacetylmesaconine (VII);

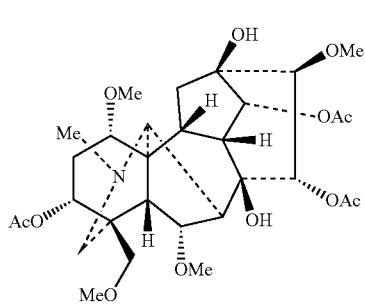
(VII)

or
dissolving N-desethyl-3,8,13,14,15-pentaacetyl aconine (VI) in tetrahydrofuran, reacting with 12 moles of 40% formaldehyde aqueous solution and 1 to 2 moles of glacial acetic acid at room temperature under stirring for 30 to 60 minutes, adding 2 to 3 moles of sodium triacetoxyborohydride, stirring at room temperature for 30 to 60 minutes, adjusting to pH 9 to 10 with strong aqua ammonia, diluting by adding water, then extracting with dichloromethane, combining the dichloromethane extracts, and then drying over anhydrous sodium sulfate, and concentrating under reduced pressure in sequence to obtain 3,8,13,14,15-pentaacetylmesaconine (VIII);

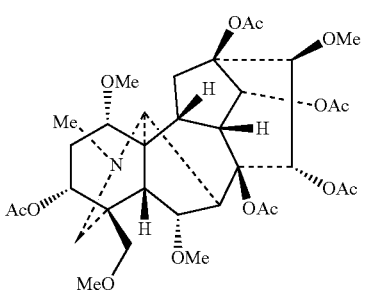
(VIII)

6) hydrolyzing 3,14,15-triacetylmesaconine (VII) or 3,8,13,14,15-pentaacetylmesaconine (VIII) by 5% to 10% sodium hydroxide ethanol solution, and adjusting to pH 4 to 5 with concentrated hydrochloric acid, then adjusting to pH 9 to 12 with a diluted solution of sodium hydroxide in ethanol, filtering off the insoluble matter, concentrating under reduced pressure, dissolving the residue with dichloromethane/anhydrous ethanol (9:1, V/V), filtering with suction, and concentrating the filtrate under reduced pressure to obtain mesaconine (IX)

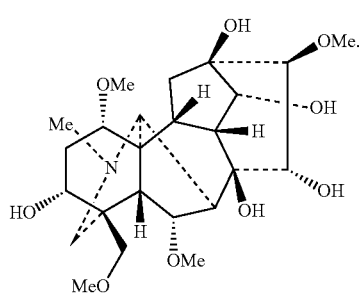

(IX)

The invention also provides intermediates used in the method for preparing mesaconine, details are as follows:

N-desethyl-3,14,15-triacetyl aconine, its structural formula is shown as formula (V)

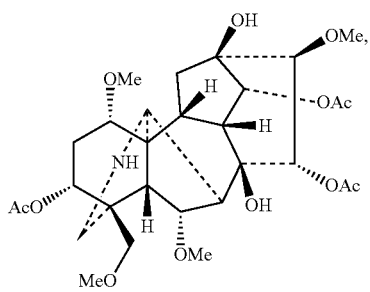

(V)

N-desethyl-3,8,13,14,15-pentaacetyl aconine, its structural formula is shown as formula (VI)

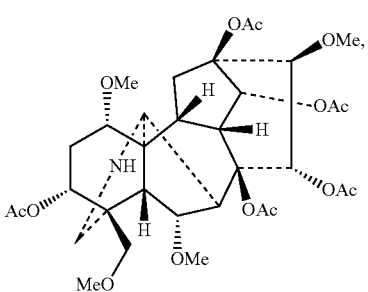

(VI)

3,14,15-triacetylmesaconine, its structural formula is shown as formula (VII)

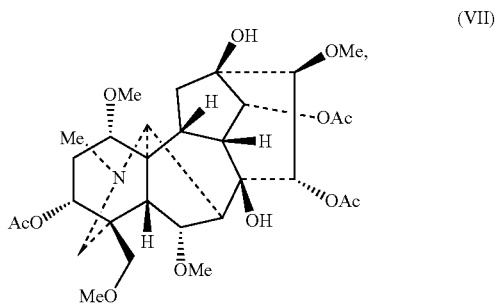

(VII)

3,8,13,14,15-pentaacetylmesaconine, its structural formula is shown as formula (VIII)

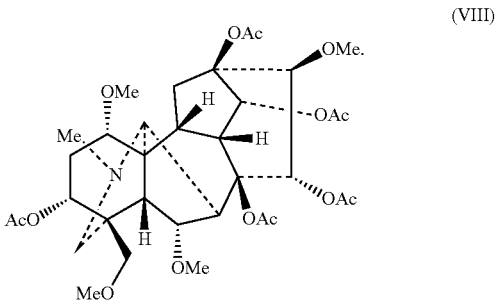

(VIII)

The aconitine in the total alkaloids has certain toxicity. In the method for preparing mesaconine of the present invention, the use of toxic intermediates is avoided and the production safety is ensured, by first hydrolyzing the benzoyl group in the aconitine (I) in the total alkaloids to obtain a non-toxic intermediate of formula II (aconine), and followed by acetylation, N-deethylation, and N-methylation in sequence to obtain non-toxic intermediate of formula III (3,14,15-triacetyl aconine), intermediate of formula IV (3,8,13,14,15-pentaacetyl aconine), intermediate of formula V (N-desethyl-3,14,15-triacetyl aconine), intermediate of formula VI (N-desethyl-3,8,13,14,15-pentaacetyl aconine), intermediate of formula VII (3,14,15-triacetylmesaconine) and intermediate of formula VIII (3,8,13,14,15-pentaacetylmesaconine) respectively. The above intermediates used in the preparation method of mesaconine of the present invention are not only non-toxic, but also make the process simple in operation and with good purification effect.

EMBODIMENTS

The following examples will further explain the present invention, however, they do not constitute a restriction or limitation on the scope of the present invention.

EXAMPLE 1

Extraction of Total Alkaloids from *Aconitum soongaricum Stapf.* of Aconitum Plant (1) 10 kg of dried roots of *Aconitum soongaricum Stapf.* were taken, crushed and sifted through a 20-mesh sieve;

(2) the powder of *Aconitum soongaricum Stapf.* of aconitum plant was extracted for 3 times in reflux with 80 L, 36 L and 24 L of an aqueous solution of 5% sulfuric acid and 85% ethanol, extracted for 2 hours each time, filtered and combined the filtrate;

(3) the filtrate was concentrated under reduced pressure, ethanol was recovered until the relative density of the fluid extract was 1.05 to 1.10, and 0.46 kg fluid extract was collected;

(4) the fluid extract was diluted by adding 1.4 L of water, alkalized with aqua ammonia, adjusted to pH 10, placed in an extractor and extracted with ethyl acetate (2 L×3 times), stirred for 5 to 10 minutes each time, and the extract was collected;

(5) ethyl acetate was recovered by concentration under reduced pressure, and 129 g total alkaloids were obtained. The total alkaloids were sampled and the content of aconitine in total alkaloids was determined by HPLC method. The total amount of aconitine (I) in the total alkaloids was calculated to be about 42.5 g based on its content in the total alkaloids and wet weight of the total alkaloids, and the yield was about 0.42%.

EXAMPLE 2

Preparation of Mesaconine (1) Preparation of aconine (II)

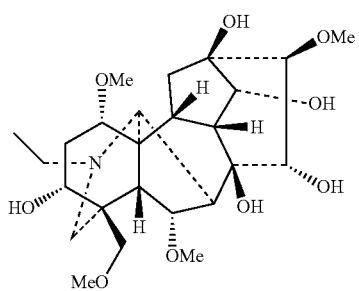

(II)

100 g total alkaloids (including 33 g of aconitine) were taken and dissolved with 500 mL of 95% ethanol, then 7.2 g (78 mmol) of sodium hydroxide was added thereto, the mixture was stirred for 2 hours at room temperature, and the solvent was recovered under reduced pressure to obtain 120 g of solid. The solid was diluted with 1000 mL of water, and extracted with dichloromethane (500 mL×2). The aqueous layer was adjusted to pH 5 with concentrated hydrochloric acid, and then adjusted to pH 11 to 12 with a diluted solution of sodium hydroxide in ethanol, and concentrated to dryness under reduced pressure to obtain 90 g of solid, which was dissolved by heating in 900 mL of dichloromethane-absolute ethanol (9:1, V/V),=, filtered, and the filtrate was concentrated under reduced pressure and a solid (22.5 g) was obtained as the desired compound.

Yield: 86%, white amorphous powder, $C_{25}H_{41}NO_9$.

$^1$H NMR (400 MHz, $CD_3OD$) δ: 0.99(3H, t, $NCH_2CH_3$), 1.86-1.97(6H, m), 2.23-2.28(2H, m), 2.33-2.38(4H, m), 2.48 (2H, m), 2.70(2H, m), 2.76(1H, d, J=6.8 Hz), 2.88-2.98(2H, m), 3.06(1H, t, J=6.8 Hz), 3.10(1H, s), 3.15, 3.20, 3.25, 3.50(each 3H, s, 4×$OCH_3$), 3.59(1H, dd, J=12.0, 4.0 Hz, H-3β), 3.71(1H, d, J=6.8 Hz, H-15β), 3.77(1H, d, J=8.0 Hz, H-16α), 4.09(1H, d, J=8.0 Hz, H-15β), 4.32(1H, d, J=4.0 Hz, H-14β);

$^{13}$C NMR (100 MHz, $CD_3OD$) δ: 13.8(q), 35.5(t), 38.8(t), 43.1(d), 44.5(s), 47.5(d), 48.3(t), 49.5(d), 50.1(t), 50.3(d), 51.1(s), 56.2(q), 58.2(q), 59.1(q), 61.6(q), 62.1(d), 70.7(d), 75.3(t), 77.7(s), 79.5(s), 79.7(d), 82.3(d), 84.2(d), 85.0(d), 93.1(d);

ESI-MS m/z (%): 500(100)[M+H]$^+$.

(2) Preparation of 3,14,15-triacetyl aconine (III)

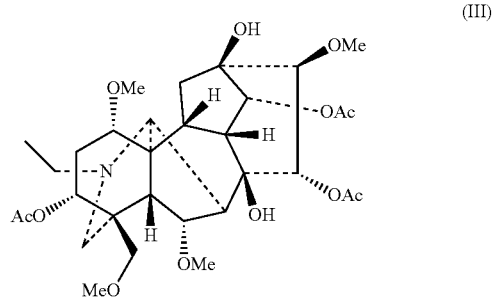

(III)

10.0 g (20 mmol) of aconine (II) was taken and mixed with 7.1 g (70 mmol) of acetic anhydride and 100 mL of pyridine, and the mixture was reacted under reflux for 2.5 hours, concentrated under reduced pressure to obtain a residue. The residue was diluted with 170 mL of water, and the diluent was alkalized to pH 9 to 10 with aqua ammonia, extracted with dichloromethane (80 ml×3). The extracts were combined, dried over anhydrous sodium sulfate, and concentrated under reduced pressure to give a solid, then the solid was subjected to silica gel column chromatography and eluted by dichloromethane-anhydrous ethanol (200:1) to obtain 10.7 g of the desired compound.

Yield: 85.6%, white amorphous powder, $C_{31}H_{47}NO_{12}$.

$^1$H NMR (400 MHz, $CDCl_3$) δ: 1.13 (3H, t, J=7.2 Hz, $NCH_2CH_3$), 1.86-1.97 (4H, m), 2.06, 2.07, 2.18 (each 3H, s, 3×OAc), 2.26, 2.54 (2H, ABq, J=6.0 Hz), 2.33-2.38 (4H, m), 2.54 (2H, m), 2.72 (2H, m), 2.88-2.94 (2H, m), 3.07 (1H, t, J=6.8 Hz), 3.20, 3.23, 3.27, 3.56 (each 3H, s, 4×$OCH_3$), 3.54 (1H, d, J=6.4 Hz), 3.91 (1H, d, J=6.0 Hz, H-16α), 4.10 (1H, d, J=4.0 Hz), 4.65 (1H, d, J=5.2, H -14β), 4.88 (1H, t, J=8.8 Hz, H-3β), 5.25 (1H, d, J=6.0 Hz, H-15β);

$^{13}$C NMR (100 MHz, $CDCl_3$) δ: 13.4(q), 20.8(q), 21.1(q), 21.1(q), 31.9(t), 36.2(t), 40.6(d), 42.0(s), 44.5(d), 45.5(d), 47.4(t), 48.9(t), 49.5(d), 49.5(s), 56.1(q), 57.8(q), 58.7(q), 60.6(d), 61.3 (q), 71.4(d), 71.7(t), 74.3(s), 76.5(s), 78.6(d), 81.7(d), 82.8(d), 87.2(d), 88.3(d), 170.1(s), 170.9(s), 173.3(s);

ESI-MS m/z (%): 626(100)[M+H]$^+$.

(3) Preparation of 3,8,13,14,15-pentaacetyl aconine (IV)

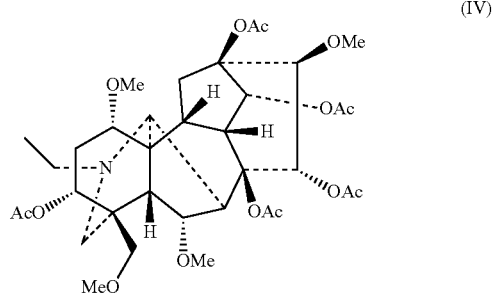

(IV)

150 mg (0.31 mmol) of aconine (II) was taken and dissolved in 1 mL of acetic anhydride, and 176 mg (0.93 mmol) of p-toluenesulfonic acid was added thereto at room temperature under stirring. The reaction solution was heated to 120° C., reacted for 3 to 4 hours, concentrated under reduced pressure to evaporate most of the solvent, the resulting residue was diluted with 20 mL of water, adjusted to pH 9 to 10 with 5 mL of aqua ammonia, and extracted with dichloromethane (10 mL×2). The extracts were combined, dried over anhydrous sodium sulfate, filtered with suction, and concentrated under reduced pressure to obtain a residue. The residue was separated by silica gel column chromatography and eluted by petroleum ether-acetone (10:1 to 2:1) to obtain 161 mg of the desired compound.

Yield: 75%, white amorphous powder, $C_{35}H_{51}NO_{14}$.

$^1$H NMR (400 MHz, CDCl$_3$) δ: 1.14 (3H, t, J=7.2 Hz, NCH$_2$CH$_3$), 1.94 (3H, s, OAc), 2.01 (1H, d, J=5.6 Hz), 2.04, 2.08 (each 3H, s, 2×OAc), 2.10, 2.13 (each 3H, s, 2×OAc), 2.25-2.54 (5H, m), 2.72-2.81(4H, m), 2.94 (1H, d, J=8.9 Hz), 3.08 (1H, dd, J=10.3, 6.9 Hz), 3.12 (1H, s), 3.19, 3.21, 3.25, 3.33 (each 3H, s, 4×OCH$_3$), 3.36 (1H, s), 3.62 (1H, dd, J=15.4, 5.3 Hz), 3.74 (1H, d, J=3.4 Hz, H-16), 3.76 (1H, s), 4.05 (1H, d, J=6.0 Hz, H-6β), 4.84 (1H, d, J=5.2 Hz, H-14β), 4.88 (1H, dd, J=12.4, 6.8 Hz, H-3β), 5.84 (1H, d, J=6.0 Hz, H-15β);

$^{13}$C NMR (100 MHz, CDCl$_3$) δ: 13.5 (q), 21.1 (q), 21.1 (q), 21.2 (q), 21.3 (q), 22.0 (q), 31.9 (t), 36.0 (t), 41.1 (d), 42.1 (s), 43.7 (d), 45.0 (d), 45.5 (d), 47.0 (t), 48.8 (t), 49.8 (s), 56.1 (q), 58.7 (q), 58.8 (q), 60.3 (q), 61.0 (d), 71.2 (t), 71.3 (d), 76.3 (d), 78.2 (d), 80.7 (s), 81.4 (d), 83.7 (d), 88.2 (d), 88.8 (s), 168.4 (s), 169.6 (s), 170.2 (s), 170.3 (s), 170.7 (s);

ESI-MS m/z (%): 710(100) [M+H]$^+$.

(4) Preparation of N-desethyl-3,14,15-triacetyl aconine (V)

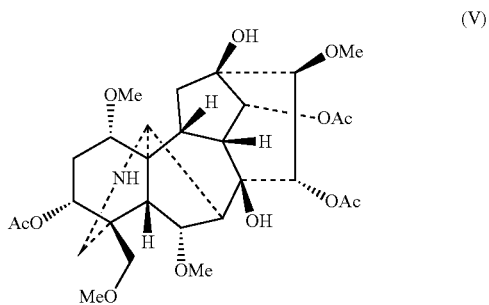

10.0 g (17 mmol) of 3,14,15-triacetyl aconine (III) was taken and dissolved in 100 mL of glacial acetic acid, 9.9 g (66 mmol) of N-bromosuccinimide was added thereto. The mixture was stirred at room temperature for 2 hours, concentrated under reduced pressure to obtain a solid. The solid was dissolved with a small amount of dichloromethane, after 150 mL of water was added, the solution was alkalized to pH 10 with strong aqua ammonia, and extracted with dichloromethane (80 ml×2). The extracts were combined, dried over anhydrous sodium sulfate, and concentrated under reduced pressure to obtain 10.5 g of solid. The solid was subjected to silica gel column chromatography and eluted by petroleum ether-acetone (2:1) to obtain 6.4 g of the desired compound.

Yield: 67.0%, white amorphous powder, $C_{29}H_{43}NO_{12}$.

$^1$H NMR (400 MHz, CDCl$_3$) δ: 1.95-1.99 (4H, m), 2.05, 2.08, 2.27 (each 3H, s, 3×OAc), 2.19-2.28 (4H, m), 2.47 (2H, m), 2.74 (1H, d, J=6.8 Hz), 2.99 (2H, m), 3.10 (1H, d, J=8.6 Hz), 3.24, 3.25, 3.29, 3.57 (each 3H, s, 4×OCH$_3$), 3.52 (1H, m), 3.68 (1H, m), 3.76 (1H, t, J=4.8 Hz), 4.10 (1H, d, J=4.0 Hz), 4.19 (1H, s), 4.68 (1H, d, J=4.8 Hz, H-14β), 5.09 (1H, t, J=6.4 Hz, H-3β), 5.25 (1H, d, J=6.4 Hz, H-15β);

$^{13}$C NMR (100 MHz, CDCl$_3$) δ: 21.0(q), 21.1(q), 21.2(q), 30.4(0, 35.1(t), 40.4(d), 41.4(t), 42.6(s), 43.3(d), 44.0(d), 49.3(t), 54.5(s), 55.2(q), 56.1(q), 57.8(q), 58.8(q), 61.4(d), 72.1(d), 74.2(t), 74.4(s), 76.7(s),78.5(d), 80.3(d), 82.6(d), 86.8(d), 87.9(d), 170.1(s), 170.7(s), 174.2(s);

ESI-MS m/z (%): 598(100)[M+H]$^+$.

(5) Preparation of N-desethyl-3,8,13,14,15-pentaacetyl aconine (VI)

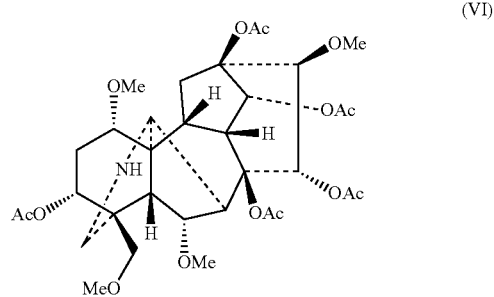

10.0 g (14 mmol) of 3,8,13,14,15-pentaacetyl aconine (IV) was taken and dissolved in 100 mL of glacial acetic acid, 9.9 g (66 mmol) of N-bromosuccinimide was added thereto. The mixture was stirred at room temperature for 2 hours, concentrated under reduced pressure to obtain a solid. The solid was dissolved with a small amount of dichloromethane, after 150 mL of water was added, the solution was alkalized to pH 10 with strong aqua ammonia, and extracted with dichloromethane (80 ml×2). The extracts were combined, dried over anhydrous sodium sulfate, and concentrated under reduced pressure to obtain 8.5 g of solid. The solid was subjected to silica gel column chromatography and eluted by petroleum ether-acetone (2:1) to obtain 6.5 g of the desired compound.

Yield: 67.7%, white amorphous powder, $C_{33}H_{47}NO_{14}$.

$^1$H NMR (400 MHz, CDCl$_3$) δ: 1.88-1.93 (2H, m), 1.94 (3H, s, OAc), 2.01-2.04 (4H, m), 2.03, 2.07 (each 3H, s, 2×OAc), 2.14, 2.16 (each 3H, s, 2×OAc), 2.27 (1H, q, J=6.4 Hz), 2.34 (1H, d, J=6.8 Hz), 2.71 (1H, dd, J=7.5, 5.4 Hz), 2.78 (1H, d, J=12.9 Hz), 2.95 (1H, d, J=8.8 Hz), 3.08 (1H, d, J=12.9 Hz), 3.15 (1H, t, J=7.1 Hz), 3.22 (3H, s, OMe), 3.26 (6H, s, 2×OMe), 3.32 (3H, s, OMe), 3.37 (1H, d, J=11.6 Hz), 3.72 (1H, d, J=8.8 Hz), 3.77 (1H, d, J=6.1 Hz), 4.06 (1H, dd, J=6.8, 1.8 Hz), 4.86 (1H, d, J=5.2 Hz, H-14β), 5.02 (1H, dd, J=9.6, 5.6 Hz, H-3β), 5.84 (1H, d, J=6.0 Hz, H-15β);

$^{13}$C NMR (100 MHz, CDCl$_3$) δ: 21.0 ($_q$), 21.1 (q), 21.3 (q), 21.3 (q), 22.1 (q), 31.6 (t), 34.7 (t), 41.1 (t), 41.2 (d), 42.7 (s), 42.8 (d), 44.5 (d), 49.3 (s), 51.4 (d), 55.7 (q), 55.8 (q), 58.7 (q), 58.8 (q), 61.1 (d), 71.8 (d), 73.0 (t), 76.3 (d), 78.2 (d), 80.5 (s), 80.6 (d), 83.8 (d), 87.8 (d), 88.4 (s), 168.3 (s), 169.7 (s), 170.3 (s), 170.4 (s), 170.6 (s);

ESI-MS m/z (%): 682 (100) [M+H]$^+$.

(6) Preparation of 3,14,15-triacetylmesaconine (VII)

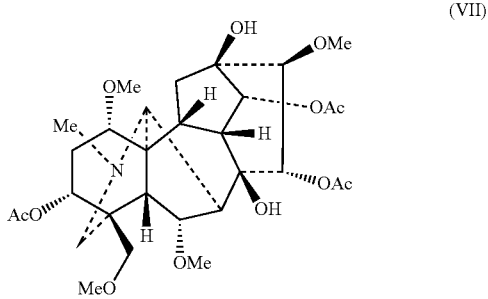

10 g (17 mmol) of N-desethyl-3,14,15-triacetyl aconine (V) was taken and dissolved in 25 mL of tetrahydrofuran, and 2 ml of 40% formaldehyde aqueous solution and 1 mL of glacial acetic acid were added at room temperature, kept stirring at this temperature for 30 minutes. Then 7.1 g (33.5 mmol) of NaBH(OAc)$_3$ was added, and continued stirring for 30 minutes. The solution was adjusted to pH 9 with strong aqua ammonia, diluted with 15 mL of water, extracted with 20 mL of dichloromethane twice. The extracts was combined, and then washed with water, dried over anhydrous sodium sulfate, and concentrated to dryness under reduced pressure in sequence to obtain 5.5 g of solid. The solid was subjected to silica gel column chromatography and eluted by chloroform-methanol (9:1) to obtain 5.41 g of the desired compound.

Yield: 53.1%, white amorphous powder, $C_{30}H_{45}NO_{12}$.

$^1$H NMR (400 MHz, CDCl$_3$) δ: 1.98-2.01 (4H, m), 2.05, 2.07, 2.21 (each 3H, s, 3×OAc), 2.22-2.30 (2H, m), 2.32 (3H, s, NCH$_3$), 2.42 (2H, m), 2.58 (1H, m), 2.63 (1H, m), 2.82 (1H, s), 2.92 (1H, m), 2.97 (1H, d, J=4.0 Hz), 3.10 (1H, dd, J=4.8 Hz), 3.20, 3.25, 3.27, 3.54 (each 3H, s, 4×OCH$_3$), 3.26 (1H, d, J=4.0 Hz), 3.95 (1H, d, J=8.0 Hz), 4.00 (1H, s), 4.13 (1H, d, J=6.0 Hz), 4.65 (1H, d, J=4.0 Hz, H-14β), 4.85 (1H, t, J=4.8 Hz, H-3β), 5.24 (1H, d, J=6.0 Hz, H-15β);

$^{13}$C NMR (100 MHz, CDCl$_3$) δ: 20.9(q), 21.0(q), 21.1(q), 31.9(t), 36.0(t), 40.7(d), 42.3(s), 42.5(q), 44.4(d), 44.8(d), 48.4(d), 49.5(s), 49.9(t), 56.5(q), 57.8(q), 58.7(q), 61.2(q), 62.0 (d), 72.1(d), 71.5(t), 74.3(s), 76.3(s),78.5(d), 81.8(d), 82.6(d), 87.2(d), 88.3(d), 170.1(s), 170.9(s), 173.4(s);

ESI-MS m/z (%): 612(100) [M+H]$^+$.

(7) Preparation of 3,8,13,14,15-pentaacetylmesaconine (VIII)

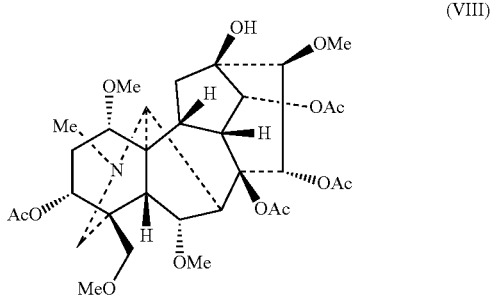

10 g (14.6 mmol) of N-desethyl-3,8,13,14,15-pentaacetyl aconine (VI) was taken and dissolved in 25 mL of tetrahydrofuran, and 2 mL of 40% formaldehyde aqueous solution and 1 mL of glacial acetic acid were added at room temperature, stirred for 30 minutes. Then 7.1 g (33.5 mmol) of NaBH(OAc)$_3$ was added, and continued stirring for 30 minutes. The solution was adjusted to pH 9 with strong aqua ammonia, diluted with 15 mL of water, extracted with 20 mL of dichloromethane twice. The extracts were combined, and then washed with water, dried over anhydrous sodium sulfate, and concentrated to dryness under reduced pressure in sequence to obtain 6.5 g of solid. The solid was subjected to silica gel column chromatography and eluted by chloroform-methanol (9:1) to obtain 6.1 g of the desired compound.

Yield: 59.8%, white amorphous powder, $C_{34}H_{49}NO_{14}$.

$^1$H NMR (400 MHz, CDCl$_3$) δ: 1.18 (1H, s), 1.95 (3H, s, OAc), 2.04, 2.08 (each 3H, s, 2×OAc), 2.14 (6H, s, 2×OAc), 2.28 (1H, d, J=6.8 Hz), 2.33-2.42 (4H, m), 2.43 (3H, s, NMe), 2.66 (1H, d, J=11.5 Hz), 2.78 (1H, dd, J=7.3, 5.4 Hz), 2.95 (1H, d, J=8.9 Hz), 3.05 (1H, s), 3.09 (1H, dd, J=10.6, 6.9 Hz), 3.19, 3.23, 3.26, 3.33 (each 3H, s, 4×OMe), 3.40 (1H, d, J=1.7 Hz), 3.62 (1H, dd, J=15.4, 5.4 Hz), 3.75 (1H, d, J=5.8 Hz), 3.77 (1H, d, J=2.9 Hz), 4.06 (1H, d, J=6.4 Hz, H-6β), 4.86 (1H, d, J=5.2 Hz, H-14β), 4.90 (1H, dd, J=12.4, 6.0 Hz, H-3β), 5.83 (1H, d, J=6.0 Hz, H-15β);

$^{13}$C NMR (100 MHz, CDCl$_3$) δ: 21.1 (q), 21.3 (q), 21.3 (q), 22.0 (q), 26.9 (q), 31.9 (t), 35.8 (t), 41.2 (q), 42.4 (s), 42.7(d), 43.8 (d), 44.1 (d), 44.8 (d), 49.6 (t), 49.9 (s), 56.4 (q), 58.7 (q), 58.8 (q), 60.9 (q), 61.9 (d), 71.1 (t), 71.2 (d), 76.3 (d), 78.3 (d), 80.7 (s), 81.5 (d), 83.6 (d), 88.2 (d), 88.7 (s), 168.4 (s), 169.5 (s), 170.1 (s), 170.2 (s), 170.7 (s);

ESI-MS m/z (%): 696(100)[M+H]$^+$.

(8): Preparation of Mesaconine (IX)

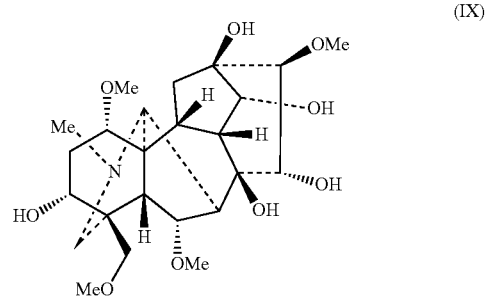

Method 1: Preparation of mesaconine (IX) from 3,14,15-triacetylmesaconine (VII) 10 g (16.3 mmol) of 3,14,15-triacetylmesaconine (VII) was taken and dissolved in 75 mL of 95% ethanol solution. Then 2.29 g (57 2 mmol) of sodium hydroxide was added, and the mixture was refluxed for 30 minutes. The reaction solution was cooled to room temperature, adjusted to pH 5 with concentrated hydrochloric acid, and then adjusted to pH 11 to 12 with a diluted solution of sodium hydroxide in ethanol. The insoluble matter was filtered off and the filtrate was concentrated under reduced pressure to obtain a solid. The solid was dissolved in 110 mL of dichloromethane-anhydrous ethanol (9:1, V/V), filtered with suction, and the filtrate was concentrated to dryness under reduced pressure to obtain 7.22 g of mesaconine, with a yield of 91.1%.

Method 2: Preparation of mesaconine (IX) from 3,8,13,14,15-pentaacetylmesaconine (VIII)

10 g (14.4 mmol) of 3,8,13,14,15-pentaacetylmesaconine (VIII) was taken and dissolved in 75 ml of 95% ethanol solution. Then 2.29 g (50.4 mmol) of sodium hydroxide was added, and the mixture was refluxed for 30 minutes. The reaction solution was cooled to room temperature, adjusted to pH 5 with concentrated hydrochloric acid, and then adjusted to pH 9 with strong aqua ammonia. The insoluble matter was filtered off and the filtrate was concentrated under reduced pressure to obtain 9.5 g of solid. The solid was dissolved in 95 mL of dichloromethane-anhydrous ethanol (9:1, V/V), filtered with suction, and the filtrate was concentrated to dryness under reduced pressure to obtain 6.2 g of mesaconine, with a yield of 90.0%.

The above mesaconine has the following physicochemical properties:

mesaconine: white solid, the specific rotation is $[\alpha]_D° +21.5$(c, 0.5,$H_2O$); the molecular formula is $C_{24}H_{39}NO_9$; easily soluble in water and methanol, soluble in ethanol, slightly soluble in isopropanol, very slightly soluble in acetone, chloroform. By sufficient two-dimensional NMR and other spectral analysis, the structural formula is determined as formula (IX)

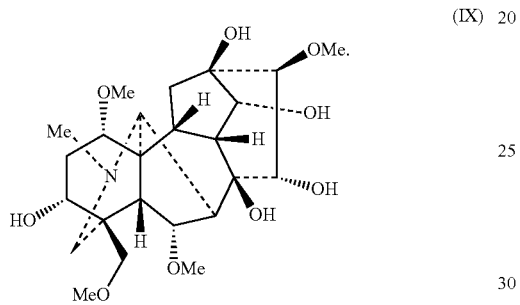

(IX)

The spectral data of mesaconine is as follows:

IR(KBr): 3424 $cm^{-1}$, 2932 $cm^{-1}$, 2892 $cm^{-1}$, 2821 $cm^{-1}$, 1639 $cm^{-1}$, 1453 $cm^{-1}$, 1106 $cm^{-1}$;

$^1$H NMR (400 MHz, $CD_3OD$) δ: 4.47(1H, d, J=6.0 Hz, H-15β), 4.24(1H, d, J=6.8 Hz, H-6β), 3.94, 3.51(2H, 2×ABq, J=8.4 Hz, $H_2$-18), 3.85(1H, d, J=5.2 Hz, H-14β), 3.71(1H, dd, J=11.2, 5.2 Hz, H-3β), 3.64(3H, s, $OCH_3$-16), 3.40(3H, s, $OCH_3$-6), 3.35(3H, s, $OCH_3$-18), 3.31(3H, s, $OCH_3$-1), 3.15(1H, dd, J=11.2, 6.8 Hz, H-1β), 3.08(1H, d, J=6.0 Hz, H-16), 2.96(1H, s, H-17), 2.71, 1.97(2H, 2×ABq, J=8.8 Hz, $H_2$-12), 2.65, 2.42(2H, 2×ABq, J=11.2 Hz, $H_2$-19), 2.38(1H, s, H-7), 2.35(3H, s, $CH_3$N-21), 2.31, 2.24(2H, m, $H_2$-2), 2.27(1H, m, H-9β), 2.11(1H, d, J=6.8 Hz, H-5β), 1.98(1H, m, H-10β);

$^{13}$C NMR (100 MHz, $CD_3OD$) δ: 82.6(C-1), 33.8(C-2), 71.5(C-3), 43.4(C-4), 46.5(C-5), 83.2(C-6), 46.4(C-7), 78.8(C-8), 48.8(C-9), 41.6(C-10), 50.1(C-11), 36.9(C-12), 76.3(C-13), 78.7(C-14), 81.5(C-15), 90.7(C-16), 62.5(C-17), 76.8(C-18), 49.8(C-19), 42.5($NCH_3$), 56.3($OCH_3$-1), 57.9($OCH_3$-6), 61.3($OCH_3$-16), 59.1($OCH_3$-18);

ESI-MS m/z (%): 486(100)$[M+H]^+$;

HR-ESI-MS: The measured value of quasi-molecular weight is 486.2699, and the calculated value is 486.2644.

The invention claimed is:

1. A method for preparing mesaconine, comprising the following steps:

1) dissolving aconitine (I) in ethanol, adding sodium hydroxide thereto to hydrolyze, concentrating under reduced pressure, and diluting the residue with water, extracting with dichloromethane to remove impurity alkaloids, acidifying the alkaline aqueous solution with hydrochloric acid, adjusting to pH 11 to 12 by aqua ammonia or a solution of sodium hydroxide in ethanol, concentrating under reduced pressure to dryness, dissolving the residue with dichloromethane-ethanol, filtering, and concentrating the filtrate under reduced pressure to obtain aconine (II);

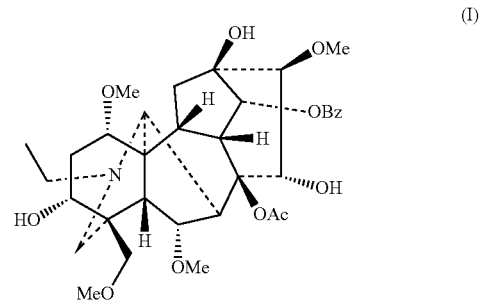

(I)

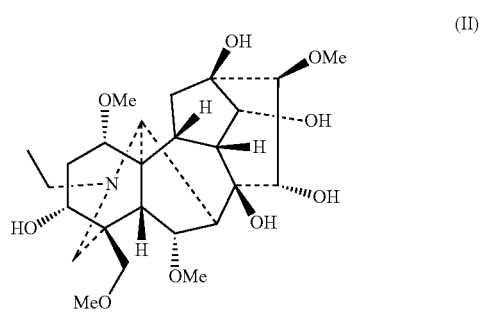

(II)

2) dissolving aconine (II) in pyridine and reacting with acetic anhydride, concentrating under reduced pressure to obtain a residue, diluting the residue with water, alkalizing with aqua ammonia, extracting with dichloromethane, combining dichloromethane layers, and then drying, concentrating, and separating by silica-gel column chromatography in sequence to prepare 3,14,15-triacetyl aconine (III);

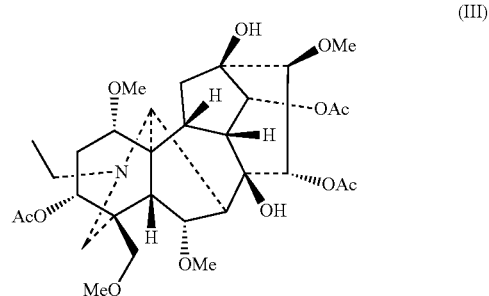

(III)

or reacting aconine (II) with acetic anhydride under the catalysis of p-toluene sulfonic acid, concentrating under reduced pressure to obtain a residue, diluting the residue with water, alkalizing with aqua ammonia, extracting with dichloromethane, combining dichloromethane layers, and then drying, concentrating, and separating by silica-gel column chromatography in sequence to prepare 3,8,13,14,15-pentaacetyl aconine (IV);

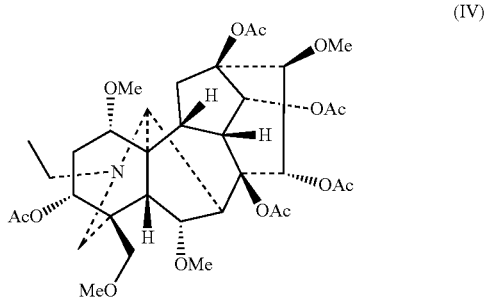

(IV)

3) dissolving 3,14,15-triacetyl aconine (III) in glacial acetic acid, adding N-bromosuccinimide thereto, stirring at room temperature, concentrating under reduced pressure to obtain a residue, adding aqua ammonia to the residue, extracting with dichloromethane, combining dichloromethane extracts, drying, and concentrating under reduced pressure to prepare N-desethyl-3,14,15-triacetyl aconine (V);

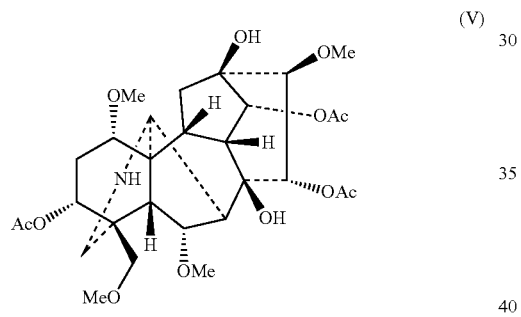

(V)

or dissolving 3,8,13,14,15-pentaacetyl aconine (IV) in glacial acetic acid, adding N-bromosuccinimide thereto, stirring at room temperature, concentrating under reduced pressure to obtain a residue, adding aqua ammonia to the residue, extracting with dichloromethane, combining dichloromethane extracts, drying, and concentrating under reduced pressure to prepare N-desethyl-3,8,13,14,15-pentaacetyl aconine (VI);

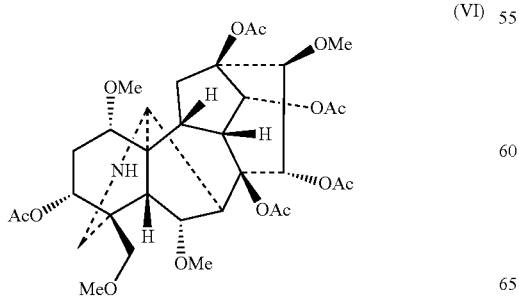

(VI)

4) dissolving N-desethyl-3,14,15-triacetyl aconine (V) in tetrahydrofuran, adding formaldehyde aqueous solution and glacial acetic acid thereto at room temperature, stirring at room temperature, adding NaBH(OAc)$_3$, continuing to stir, adding aqua ammonia, diluting with water, then extracting with dichloromethane, combining the dichloromethane extracts, and then washing with water, drying, and concentrating under reduced pressure in sequence to prepare 3,14,15-triacetylmesaconine (VII);

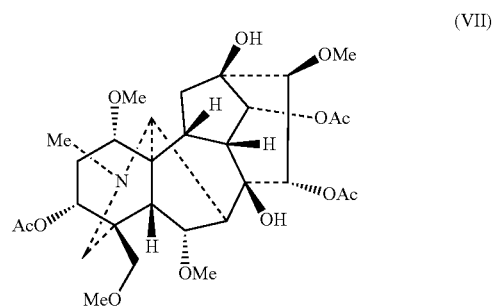

(VII)

or dissolving N-desethyl-3,8,13,14,15-pentaacetyl aconine (VI) in tetrahydrofuran, adding formaldehyde aqueous solution and glacial acetic acid thereto at room temperature, stirring at room temperature, adding NaBH(OAc)$_3$, continuing to stir, adding aqua ammonia, diluting with water, extracting with dichloromethane, combining the dichloromethane extracts, and then washing with water, drying, and concentrating under reduced pressure in sequence to prepare 3,8,13,14,15-pentaacetylmesaconine (VIII);

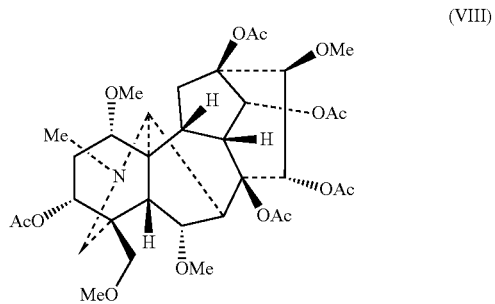

(VIII)

5) dissolving 3,14,15-triacetylmesaconine (VII) or 3,8,13,14,15-pentaacetylmesaconine (VIII) in ethanol solution, adding sodium hydroxide to react with the mesaconine derivative respectively, adjusting to pH 4 to 5 with hydrochloric acid, then adjusting to pH 9 to 12 with aqua ammonia or a solution of sodium hydroxide in ethanol, filtering off insoluble materials, concentrating under reduced pressure, dissolving the residue with dichloromethane-ethanol, filtering with suction, and concentrating the filtrate under reduced pressure to obtain mesaconine (IX)

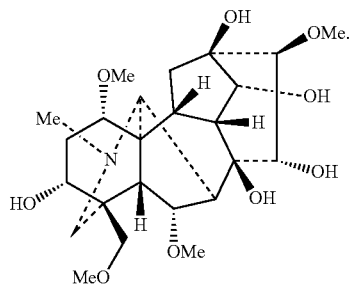

(IX)

2. The method according to claim 1, wherein the aconitine (I) is prepared by the following method:

after crushing the roots of the aconitum plant, adding sulfuric acid-ethanol aqueous solution to extract under reflux; concentrating the extract under reduced pressure to obtain a solid extract; diluting the solid extract with water, and after alkalization, extracting with ethyl acetate, and recovering the solvent to obtain an ethyl acetate extract; subjecting the ethyl acetate extract to acid dissolution, filtration, and alkalization and precipitation to obtain the aconitine (I).

3. The method according to claim 2, wherein the content of sulfuric acid is 1-10% and the content of ethanol is 80-90%, based on the total mass of the sulfuric acid-ethanol aqueous solution.

4. The method according to claim 2, wherein the content of sulfuric acid is 5% and the content of ethanol is 85%, based on the total mass of the sulfuric acid-ethanol aqueous solution.

5. The method according to claim 2, wherein the aconitum plant is *Aconitum soongaricum Stapf.* or *Aconitum karakolicum Rapaics.*

6. N-desethyl-3,14,15-triacetyl aconine, its structural formula is shown as formula (V)

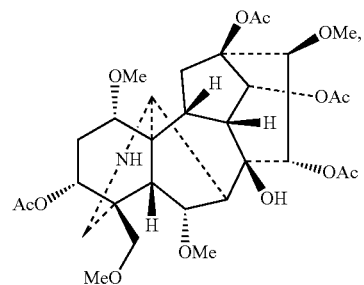

(V)

or
N-desethyl-3,8,13,14,15-pentaacetyl aconine, its structural formula is shown as formula (VI)

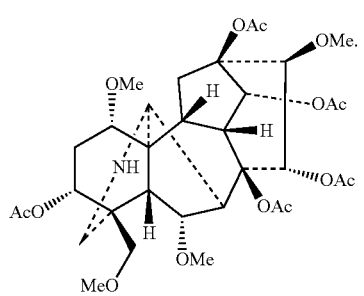

(VI)

7. 3,14,15-triacetylmesaconine, its structural formula is shown as formula (VII)

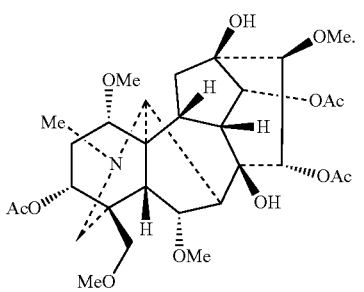

(VII)

8. The method according to claim 3, wherein the content of sulfuric acid is 5% and the content of ethanol is 85%, based on the total mass of the sulfuric acid-ethanol aqueous solution.

* * * * *